(12) United States Patent
George et al.

(10) Patent No.: US 11,744,580 B2
(45) Date of Patent: Sep. 5, 2023

(54) LONG STAPLER RELOADS WITH CONTINUOUS CARTRIDGE

(71) Applicant: Covidien LP, Mansfield, MA (US)

(72) Inventors: Sabastian K. George, Hyderabad (IN); Logamurugaraj Shanmugavel, Hyderabad (IN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/103,054

(22) Filed: Nov. 24, 2020

(65) Prior Publication Data
US 2022/0160352 A1    May 26, 2022

(51) Int. Cl.
*A61B 17/068*    (2006.01)
*A61B 17/072*    (2006.01)

(52) U.S. Cl.
CPC ........ *A61B 17/0686* (2013.01); *A61B 17/072* (2013.01); *A61B 2017/07264* (2013.01); *A61B 2017/07271* (2013.01)

(58) Field of Classification Search
CPC ...... A61B 17/07207; A61B 2017/2926; A61B 2017/2932; A61B 2017/2947; A61B 2017/07271
See application file for complete search history.

(56) References Cited

U.S. PATENT DOCUMENTS

| | | |
|---|---|---|
| 37,165 A | 12/1862 | Gary |
| 3,209,754 A | 10/1965 | Brown |
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Nolles |
| 4,204,623 A | 5/1980 | Green |
| 4,217,902 A | 8/1980 | March |
| 4,263,903 A | 4/1981 | Griggs |
| 4,275,813 A | 6/1981 | Noiles |

(Continued)

FOREIGN PATENT DOCUMENTS

| | | |
|---|---|---|
| CN | 101683284 A | 3/2010 |
| CN | 102648864 A | 8/2012 |

(Continued)

OTHER PUBLICATIONS

Detemple, P., "Microtechnology in Modern Health Care", Med Device Technol. 9(9):18-25 (1998).

(Continued)

*Primary Examiner* — Andrew M Tecco
*Assistant Examiner* — Jacob A Smith
(74) *Attorney, Agent, or Firm* — Carter, DeLuca & Farrell LLP

(57) ABSTRACT

An end effector for a surgical stapling apparatus includes a cartridge assembly and an anvil assembly. The cartridge assembly includes a cartridge channel supporting a reload. The reload includes a plurality of separate and distinct cartridge units that removably interconnect with one another within the cartridge channel. The cartridge assembly can include a cartridge channel that supports the reload and a hinge assembly that pivotally couples to the cartridge channel.

16 Claims, 13 Drawing Sheets

(56) References Cited

U.S. PATENT DOCUMENTS

| | | |
|---|---|---|
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |

(56) References Cited

U.S. PATENT DOCUMENTS

| | | | |
|---|---|---|---|
| 5,829,662 | A | 11/1998 | Allen et al. |
| 5,830,121 | A | 11/1998 | Enomoto et al. |
| 5,849,023 | A | 12/1998 | Mericle |
| 5,849,028 | A | 12/1998 | Chen |
| 5,855,311 | A | 1/1999 | Hamblin et al. |
| 5,861,005 | A | 1/1999 | Kontos |
| 5,865,361 | A | 2/1999 | Milliman et al. |
| 5,876,401 | A | 3/1999 | Schulze et al. |
| 5,891,156 | A | 4/1999 | Gessner et al. |
| 5,893,813 | A | 4/1999 | Yamamoto |
| 5,895,396 | A | 4/1999 | Day et al. |
| 5,906,607 | A | 5/1999 | Taylor et al. |
| 5,911,721 | A | 6/1999 | Nicholson et al. |
| 5,918,791 | A | 7/1999 | Sorrentino et al. |
| 5,928,222 | A | 7/1999 | Kleinerman |
| 5,944,717 | A | 8/1999 | Lee et al. |
| 5,944,736 | A | 8/1999 | Taylor et al. |
| 5,954,259 | A | 9/1999 | Viola et al. |
| 5,961,521 | A | 10/1999 | Roger |
| 5,964,394 | A | 10/1999 | Robertson |
| 5,968,044 | A | 10/1999 | Nicholson et al. |
| 5,976,171 | A | 11/1999 | Taylor |
| 5,980,518 | A | 11/1999 | Carr et al. |
| 5,980,548 | A | 11/1999 | Evans et al. |
| 5,991,355 | A | 11/1999 | Dahlke |
| 5,991,650 | A | 11/1999 | Swanson et al. |
| 5,992,724 | A | 11/1999 | Snyder |
| 5,997,552 | A | 12/1999 | Person et al. |
| 6,004,335 | A | 12/1999 | Vaitekunas et al. |
| 6,007,550 | A | 12/1999 | Wang et al. |
| 6,010,054 | A | 1/2000 | Johnson et al. |
| 6,013,077 | A | 1/2000 | Harwin |
| 6,015,417 | A | 1/2000 | Reynolds, Jr. |
| 6,017,354 | A | 1/2000 | Culp et al. |
| 6,030,410 | A | 2/2000 | Zurbrugg |
| 6,032,849 | A | 3/2000 | Mastri et al. |
| 6,039,731 | A | 3/2000 | Taylor et al. |
| 6,051,007 | A | 4/2000 | Hogendijk et al. |
| 6,063,078 | A | 5/2000 | Wittkampf |
| 6,063,095 | A | 5/2000 | Wang et al. |
| 6,077,246 | A | 6/2000 | Kullas et al. |
| 6,079,606 | A | 6/2000 | Milliman et al. |
| 6,080,150 | A | 6/2000 | Gough |
| 6,083,242 | A | 7/2000 | Cook |
| 6,090,123 | A | 7/2000 | Culp et al. |
| 6,092,422 | A | 7/2000 | Binnig et al. |
| 6,109,500 | A | 8/2000 | Alli et al. |
| 6,113,592 | A | 9/2000 | Taylor |
| 6,123,702 | A | 9/2000 | Swanson et al. |
| H1904 | H | 10/2000 | Yates et al. |
| 6,126,058 | A | 10/2000 | Adams et al. |
| 6,126,651 | A | 10/2000 | Mayer |
| 6,127,811 | A | 10/2000 | Shenoy et al. |
| 6,132,425 | A | 10/2000 | Gough |
| 6,165,169 | A | 12/2000 | Panescu et al. |
| 6,166,538 | A | 12/2000 | D'Alfonso |
| 6,179,840 | B1 | 1/2001 | Bowman |
| 6,187,009 | B1 | 2/2001 | Herzog et al. |
| 6,187,019 | B1 | 2/2001 | Stefanchik et al. |
| 6,190,401 | B1 | 2/2001 | Green et al. |
| 6,193,501 | B1 | 2/2001 | Masel et al. |
| 6,202,914 | B1 | 3/2001 | Geiste et al. |
| 6,217,573 | B1 | 4/2001 | Webster |
| 6,228,534 | B1 | 5/2001 | Takeuchi et al. |
| 6,231,565 | B1 | 5/2001 | Tovey et al. |
| 6,236,874 | B1 | 5/2001 | Devlin et al. |
| 6,237,604 | B1 | 5/2001 | Burnside et al. |
| 6,241,139 | B1 | 6/2001 | Milliman et al. |
| 6,245,065 | B1 | 6/2001 | Panescu et al. |
| 6,248,117 | B1 | 6/2001 | Blatter |
| 6,250,532 | B1 | 6/2001 | Green et al. |
| 6,258,111 | B1 | 7/2001 | Ross et al. |
| 6,264,086 | B1 | 7/2001 | McGuckin, Jr. |
| 6,264,087 | B1 | 7/2001 | Whitman |
| 6,264,653 | B1 | 7/2001 | Falwell |
| 6,281,471 | B1 | 8/2001 | Smart |
| 6,288,534 | B1 | 9/2001 | Starkweather et al. |
| 6,290,701 | B1 | 9/2001 | Enayati |
| 6,293,943 | B1 | 9/2001 | Panescu et al. |
| 6,295,330 | B1 | 9/2001 | Skog et al. |
| 6,315,184 | B1 | 11/2001 | Whitman |
| 6,329,778 | B1 | 12/2001 | Culp et al. |
| 6,330,965 | B1 | 12/2001 | Milliman et al. |
| 6,346,104 | B2 | 2/2002 | Daly et al. |
| 6,355,066 | B1 | 3/2002 | Kim |
| 6,364,884 | B1 | 4/2002 | Bowman et al. |
| 6,387,092 | B1 | 5/2002 | Burnside et al. |
| 6,388,240 | B2 | 5/2002 | Schulz et al. |
| 6,402,766 | B2 | 6/2002 | Bowman et al. |
| H2037 | H | 7/2002 | Yates et al. |
| 6,412,279 | B1 | 7/2002 | Coleman et al. |
| 6,425,903 | B1 | 7/2002 | Voegele |
| 6,436,097 | B1 | 8/2002 | Nardella |
| 6,436,107 | B1 | 8/2002 | Wang et al. |
| 6,436,110 | B2 | 8/2002 | Bowman et al. |
| 6,443,973 | B1 | 9/2002 | Whitman |
| 6,447,517 | B1 | 9/2002 | Bowman |
| 6,461,372 | B1 | 10/2002 | Jensen et al. |
| 6,478,210 | B2 | 11/2002 | Adams et al. |
| 6,497,707 | B1 | 12/2002 | Bowman et al. |
| 6,505,768 | B2 | 1/2003 | Whitman |
| 6,515,273 | B2 | 2/2003 | Al-Ali |
| 6,524,316 | B1 | 2/2003 | Nicholson et al. |
| 6,533,157 | B1 | 3/2003 | Whitman |
| 6,540,751 | B2 | 4/2003 | Enayati |
| 6,544,273 | B1 | 4/2003 | Harari et al. |
| 6,554,852 | B1 | 4/2003 | Oberlander |
| 6,562,071 | B2 | 5/2003 | Jarvinen |
| 6,578,579 | B2 | 6/2003 | Burnside et al. |
| 6,601,748 | B1 | 8/2003 | Fung et al. |
| 6,601,749 | B2 | 8/2003 | Sullivan et al. |
| 6,602,252 | B2 | 8/2003 | Mollenauer |
| 6,611,793 | B1 | 8/2003 | Burnside et al. |
| 6,616,821 | B2 | 9/2003 | Broadley et al. |
| 6,629,986 | B1 | 10/2003 | Ross et al. |
| 6,651,669 | B1 | 11/2003 | Burnside |
| 6,656,177 | B2 | 12/2003 | Truckai et al. |
| 6,669,073 | B2 | 12/2003 | Milliman et al. |
| 6,669,705 | B2 | 12/2003 | Westhaver et al. |
| 6,696,008 | B2 | 2/2004 | Brandinger |
| 6,698,643 | B2 | 3/2004 | Whitman |
| 6,699,177 | B1 | 3/2004 | Wang et al. |
| 6,716,233 | B1 | 4/2004 | Whitman |
| 6,736,085 | B1 | 5/2004 | Esnouf |
| 6,792,390 | B1 | 9/2004 | Burnside et al. |
| 6,793,652 | B1 | 9/2004 | Whitman et al. |
| 6,817,508 | B1 | 11/2004 | Racenet et al. |
| 6,830,174 | B2 | 12/2004 | Hillstead et al. |
| 6,843,403 | B2 | 1/2005 | Whitman |
| 6,846,307 | B2 | 1/2005 | Whitman et al. |
| 6,846,308 | B2 | 1/2005 | Whitman et al. |
| 6,846,309 | B2 | 1/2005 | Whitman et al. |
| 6,849,071 | B2 | 2/2005 | Whitman et al. |
| 6,861,639 | B2 | 3/2005 | Al-Ali |
| 6,872,214 | B2 | 3/2005 | Sonnenschein et al. |
| 6,899,538 | B2 | 5/2005 | Matoba |
| 6,900,004 | B2 | 5/2005 | Satake |
| 6,905,057 | B2 | 6/2005 | Swayze et al. |
| 6,926,636 | B2 | 8/2005 | Luper |
| 6,953,139 | B2 | 10/2005 | Milliman et al. |
| 6,959,852 | B2 | 11/2005 | Shelton, IV et al. |
| 6,964,363 | B2 | 11/2005 | Wales et al. |
| 6,979,328 | B2 | 12/2005 | Baerveldt et al. |
| 6,981,628 | B2 | 1/2006 | Wales |
| 6,981,941 | B2 | 1/2006 | Whitman et al. |
| 6,988,649 | B2 | 1/2006 | Shelton, IV et al. |
| 7,000,819 | B2 | 2/2006 | Swayze et al. |
| 7,032,798 | B2 | 4/2006 | Whitman et al. |
| 7,044,353 | B2 | 5/2006 | Mastri et al. |
| 7,048,687 | B1 | 5/2006 | Reuss et al. |
| 7,055,731 | B2 | 6/2006 | Shelton, IV et al. |
| 7,059,508 | B2 | 6/2006 | Shelton, IV et al. |
| 7,077,856 | B2 | 7/2006 | Whitman |
| 7,083,075 | B2 | 8/2006 | Swayze et al. |

(56) References Cited

U.S. PATENT DOCUMENTS

| | | |
|---|---|---|
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 8,685,004 B2 | 4/2014 | Zemlock et al. |
| 9,192,381 B2 | 11/2015 | Marczyk |
| 9,364,222 B2 | 6/2016 | Zemlok et al. |
| 9,370,360 B2 | 6/2016 | Marczyk |
| 9,370,361 B2 | 6/2016 | Viola et al. |
| 9,433,415 B2 | 9/2016 | Marczyk et al. |
| 9,480,492 B2 | 11/2016 | Aranyi et al. |
| 9,585,659 B2 | 3/2017 | Viola et al. |
| 10,492,814 B2 | 12/2019 | Snow et al. |
| 10,722,222 B2 | 7/2020 | Aranyi |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma et al. |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |

(56) References Cited

U.S. PATENT DOCUMENTS

| | | | |
|---|---|---|---|
| 2012/0223121 A1 | 9/2012 | Viola et al. | |
| 2012/0241494 A1 | 9/2012 | Marczyk | |
| 2012/0277790 A1 | 11/2012 | Zemlok et al. | |
| 2012/0298718 A1 | 11/2012 | Marczyk | |
| 2012/0298720 A1 | 11/2012 | Marczyk | |
| 2014/0103092 A1* | 4/2014 | Kostrzewski | A61B 17/072 227/178.1 |
| 2015/0173755 A1* | 6/2015 | Baxter, III | A61B 17/072 227/180.1 |
| 2016/0256152 A1* | 9/2016 | Kostrzewski | A61B 17/42 |
| 2016/0270788 A1* | 9/2016 | Czernik | A61B 17/07207 |
| 2016/0324514 A1* | 11/2016 | Srinivas | A61B 17/00234 |
| 2016/0345973 A1* | 12/2016 | Marczyk | A61B 17/07207 |
| 2017/0172571 A1* | 6/2017 | Thompson | A61B 17/07207 |
| 2017/0290584 A1* | 10/2017 | Jasemian | A61B 17/07207 |
| 2019/0142422 A1* | 5/2019 | Kostrzewski | A61B 17/07207 227/177.1 |
| 2019/0183490 A1* | 6/2019 | Shelton, IV | A61B 17/07207 |
| 2019/0183492 A1* | 6/2019 | Shelton, IV | A61B 17/07207 |

FOREIGN PATENT DOCUMENTS

| | | |
|---|---|---|
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1813203 A2 | 8/2007 |
| FR | 2 849 589 A1 | 7/2004 |
| WO | 9414129 A1 | 6/1994 |
| WO | 9729694 A1 | 8/1997 |
| WO | 9740760 A1 | 11/1997 |
| WO | 9837825 A1 | 9/1998 |
| WO | 1999/52489 A1 | 10/1999 |
| WO | 0234140 A2 | 5/2002 |
| WO | 03026511 A1 | 4/2003 |
| WO | 03030743 A2 | 4/2003 |
| WO | 2004032760 A2 | 4/2004 |
| WO | 2007030753 A2 | 3/2007 |
| WO | 2007/114868 A2 | 10/2007 |
| WO | 2007118179 A2 | 10/2007 |
| WO | 2007014355 A3 | 4/2009 |
| WO | 2009143092 A1 | 11/2009 |

OTHER PUBLICATIONS

Abridged Data Sheet, "DeepCover Secure Authenticator with 1-Wire SHA-256 and 512-Bit User EEPROM", Maxim Integrated Products, Inc. pp. 1-4; 42; Dec. 2012.

Data Sheet "DS28E15-1-Sire SHA-256 Secure Authenticator with 512-Bit User EEPROM"; IC-On-Line, Electronic Component Manufacturers, pp. 1-2; Aug. 2013.

International Search Report and Written Opinion for Application No. PCT/US2021/058773 dated Apr. 25, 2022.

International Preliminary Report on Patentability and Written Opinion issued in corresponding International Application No. PCT/US2021/058773 dated Jun. 8, 2023, 11 pages.

\* cited by examiner

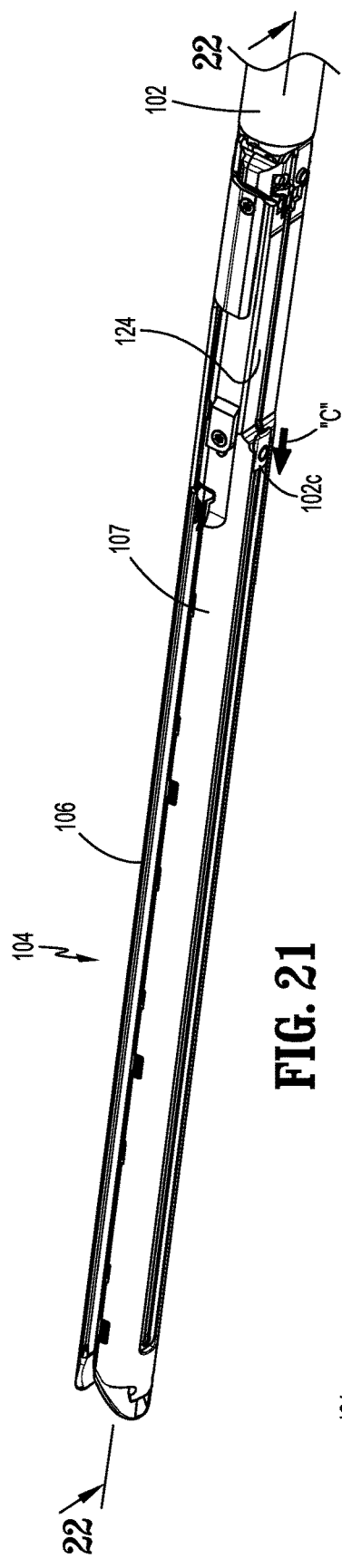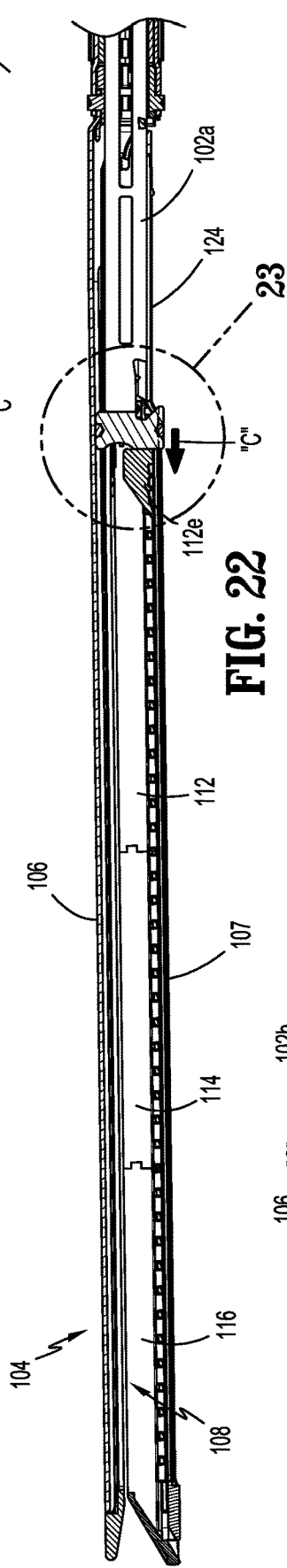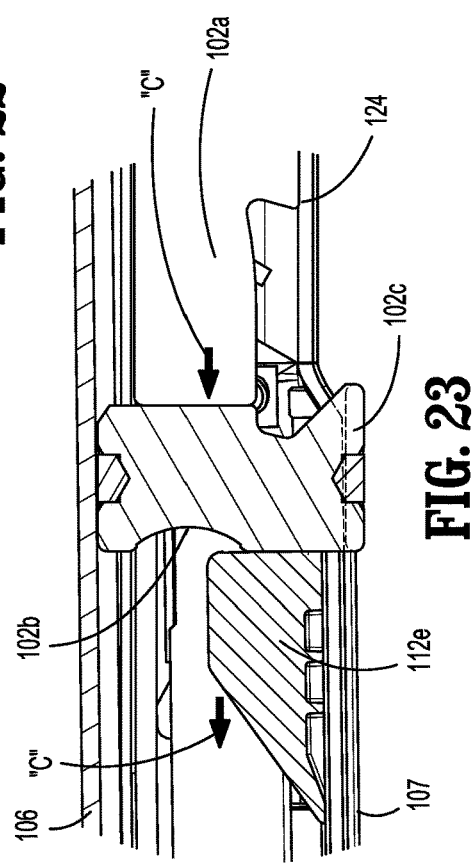

LONG STAPLER RELOADS WITH CONTINUOUS CARTRIDGE

TECHNICAL FIELD

This disclosure relates to surgical stapling apparatus, devices and/or systems for performing surgical procedures and methods of use thereof.

BACKGROUND

Surgical stapling apparatus that clamp, cut and/or staple tissue are well known in the art. Such surgical stapling apparatus include end effectors having two elongated jaw members used to capture or clamp tissue. One of the two jaw members usually carries a staple cartridge that houses a plurality of staples positioned in rows, while the other of the two jaw members has an anvil for forming the staples as the staples are driven from the staple cartridge. For instance, in linear surgical stapling apparatus, a stapling operation is effectuated by a cam bar, a drive sled or other similar mechanism having a cam member that travels longitudinally through channels defined in the staple cartridge and acts upon staple pushers in the channels to sequentially eject linear rows of staples from the staple cartridge. A knife is movably positioned between the linear rows of staples such that when the surgical stapling apparatus is positioned about tissue and actuated, the tissue is joined and/or simultaneously or nearly simultaneously cut.

SUMMARY

According to one aspect of the disclosure, a loading unit for a surgical stapling apparatus includes a shaft assembly and an end effector secured to the shaft assembly. The end effector includes an anvil assembly and a cartridge assembly. The cartridge assembly includes a cartridge channel and a hinge assembly pivotally coupled together. The hinge assembly includes one or more arms that extend between the shaft assembly and the cartridge channel to enable the cartridge assembly to move relative to the anvil assembly between an open position and a closed position.

In aspects of this disclosure, the cartridge assembly may further include a reload that is selectively attachable to the cartridge channel. The reload may include a plurality of cartridge units that selectively interconnect with one another. Each cartridge unit of the plurality of cartridge units may include a plurality of rows of staples. The plurality of cartridge units may interconnect by a tongue-and-groove arrangement. One or more cartridge units of the plurality of cartridge units may include a side lock that secures the one or more cartridge units to the cartridge channel.

In aspects of this disclosure, a spring mechanism may extend between the hinge assembly and the cartridge channel to prevent the cartridge assembly from inverting.

In aspects of this disclosure, the cartridge channel may include a stopper that is positioned to engage the hinge assembly to maintain the cartridge assembly in parallel relation to the anvil assembly.

In aspects of this disclosure, a drive beam assembly may be positioned to advance distally through the anvil and cartridge assemblies to move the cartridge assembly relative to the anvil assembly.

In aspects of this disclosure, the hinge assembly may further include one or more fasteners that connect the one or more arms to the shaft assembly. The one or more arms may be positioned to pivot about one or more fasteners.

According to another aspect of this disclosure, an end effector for a surgical stapling apparatus includes an anvil assembly and a cartridge assembly. The cartridge assembly includes a cartridge channel supporting a reload. The reload includes a plurality of separate and distinct cartridge units that removably interconnect with one another within the cartridge channel.

In aspects of this disclosure, each cartridge unit of the plurality of separate and distinct cartridge units may include a plurality of rows of staples. A first cartridge unit of the plurality of separate and distinct cartridge units may include a sled that is positioned to advance through each cartridge unit of the plurality of separate and distinct cartridge units to fire the plurality of rows of staples in each cartridge unit.

In aspects of this disclosure, a hinge assembly may be pivotally coupled to a proximal end portion of the cartridge channel. The hinge assembly may include a first arm and second arm. The first arm may be coupled to a first side of the cartridge channel by a first fastener. The second arm may be coupled to a second side of the cartridge channel by a second fastener.

In aspects of this disclosure, a first cartridge unit of the plurality of separate and distinct cartridge units may be coupled to a second cartridge unit plurality of separate and distinct cartridge units by a castellated seam. The first cartridge unit may include one or more grooves and the second cartridge unit may include one or more tongues. The one or more grooves may be positioned to receive the one or more tongues therein to define the castellated seam.

In aspects of this disclosure, each cartridge unit of the plurality of separate and distinct cartridge units may include a side lock that secures to the cartridge channel.

In aspects of this disclosure, a spring mechanism may extend between the hinge assembly and the cartridge channel to prevent the cartridge assembly from inverting.

In aspects of this disclosure, the cartridge channel may include a stopper that is positioned to engage the hinge assembly to maintain the cartridge assembly in parallel relation to the anvil assembly.

According to yet another aspect of this disclosure, a surgical stapling apparatus includes a shaft assembly defining a longitudinal axis, a drive beam assembly supported in the shaft assembly, an anvil assembly, and a cartridge assembly pivotally coupled to the anvil assembly and to the shaft assembly by a hinge assembly. The cartridge assembly supports a reload having a plurality of separate and distinct cartridge units that are independently separable from one another. Each cartridge unit of the plurality of separate and distinct cartridge units includes a plurality of staples positioned to form against the anvil assembly, wherein in response to the drive beam assembly translating through the hinge assembly, the hinge assembly pivots from a first position transverse to the longitudinal axis of the shaft assembly to a second position in parallel relation to the longitudinal axis.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate aspects of the disclosure and, together with a general description of the disclosure given above, and the detailed description of the aspect(s) given below, serve to explain the principles of the disclosure, wherein:

FIGS. 17-23 are progressive views illustrating the end effector of FIG. 1 moving from the open position to a closed position.

DETAILED DESCRIPTION

Figure 1:
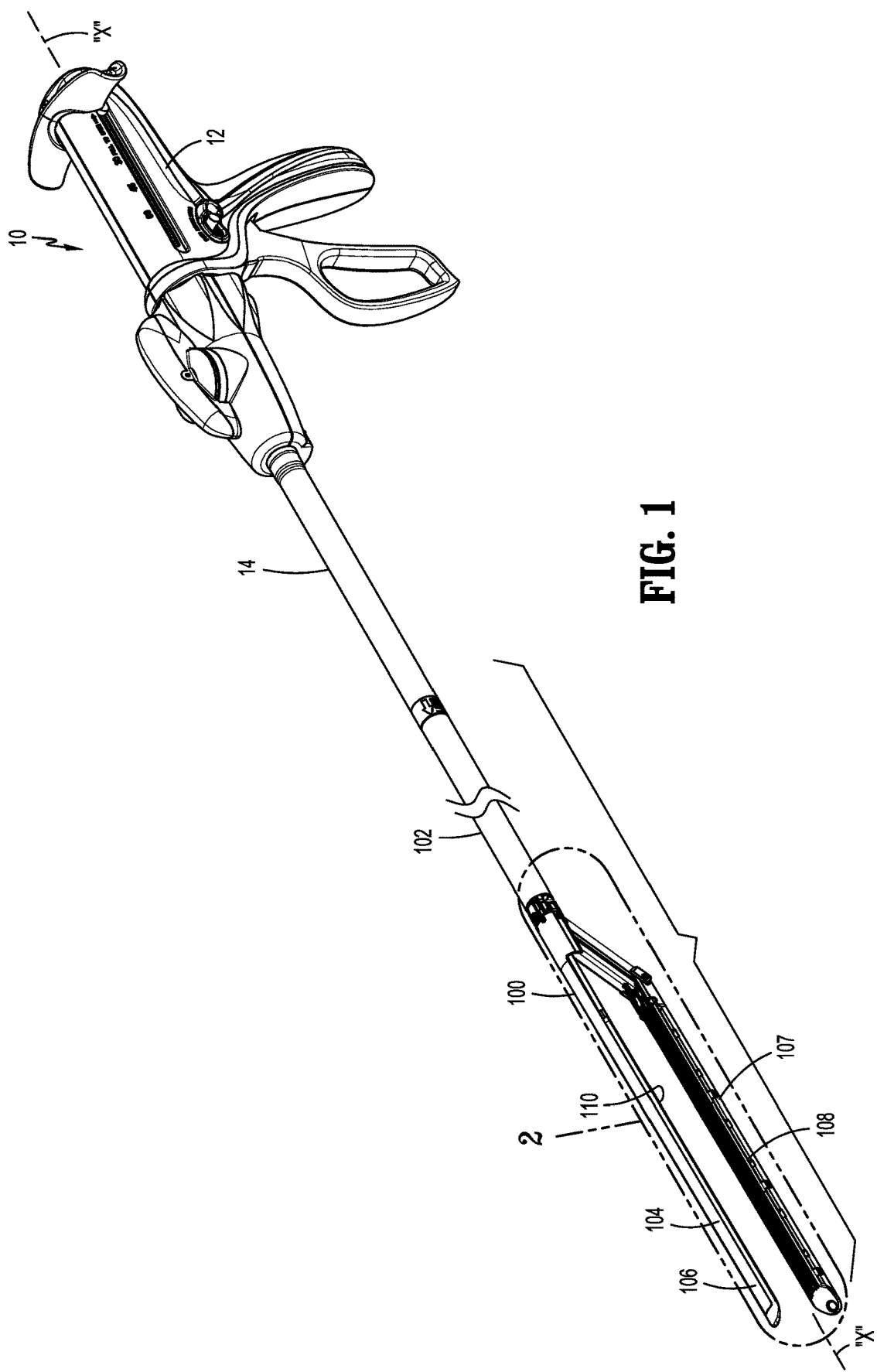
FIG. 1 is a perspective view of a surgical stapling apparatus with an end effector of a loading unit thereof in an open position in accordance with the principles of the disclosure.
Figure 2:
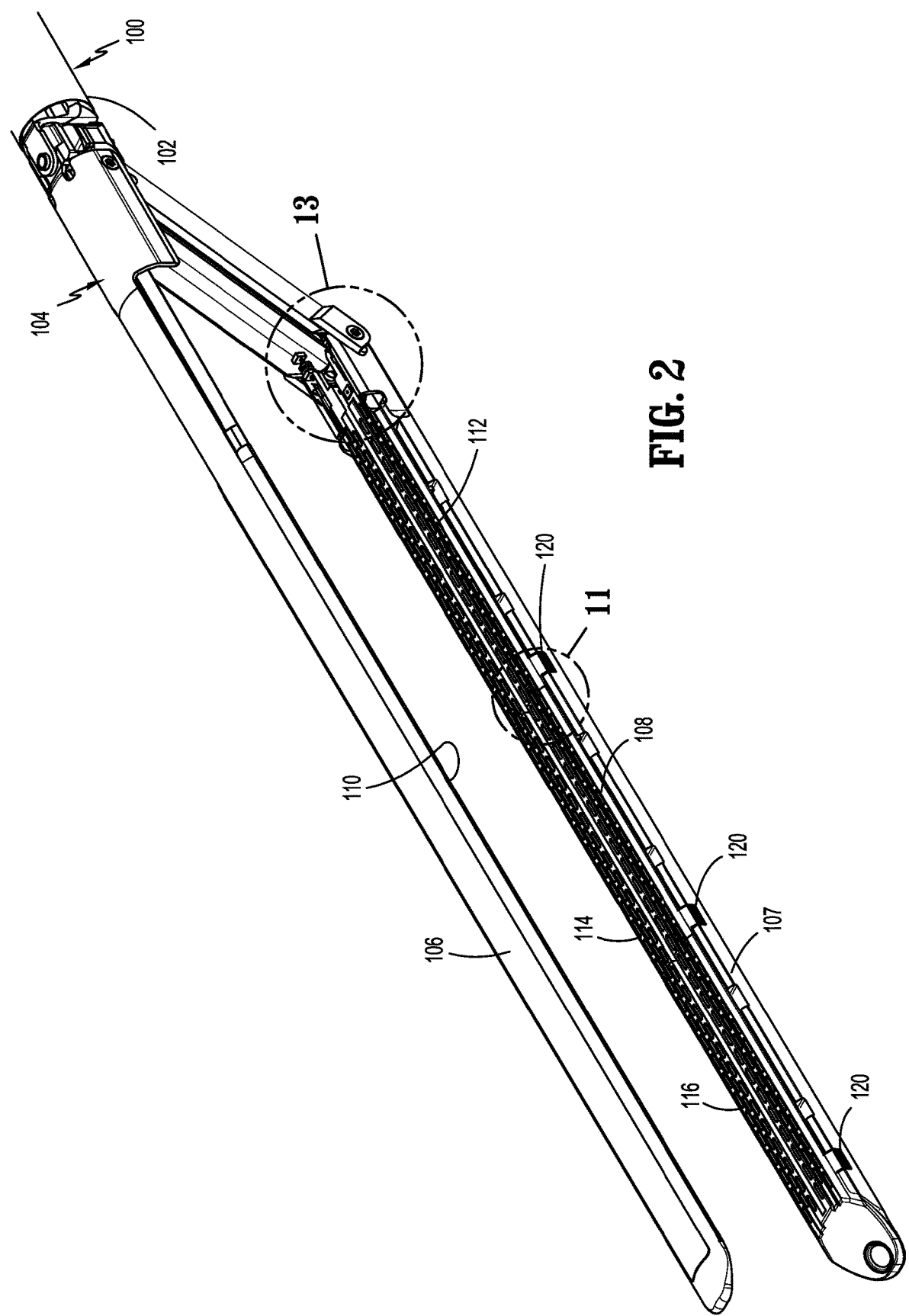
FIG. 2 is an enlarged, perspective view of the indicated area of detail shown in FIG. 1.
Figure 3:
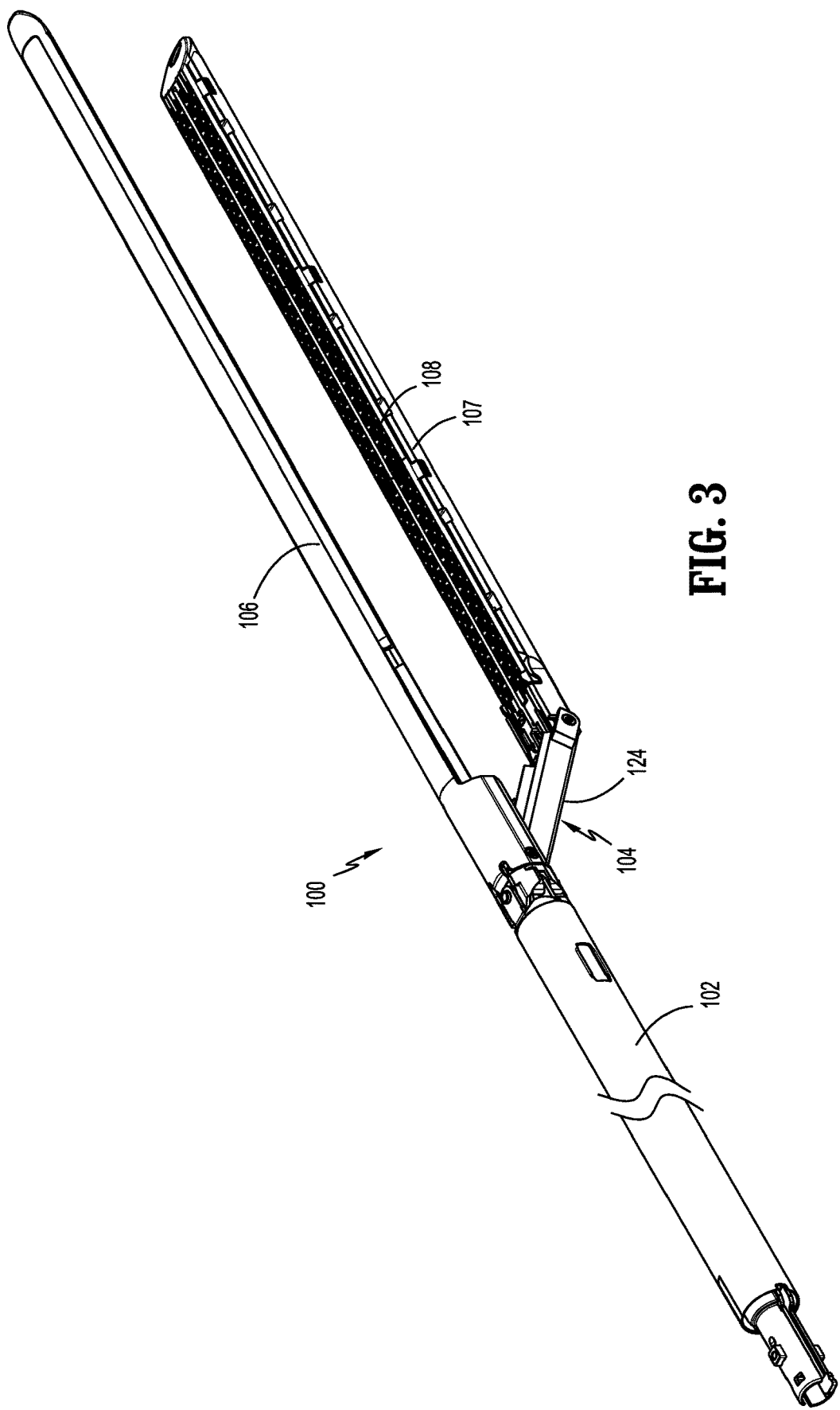
FIG. 3 is a perspective view of the reload of FIG. 1.
Figure 4:
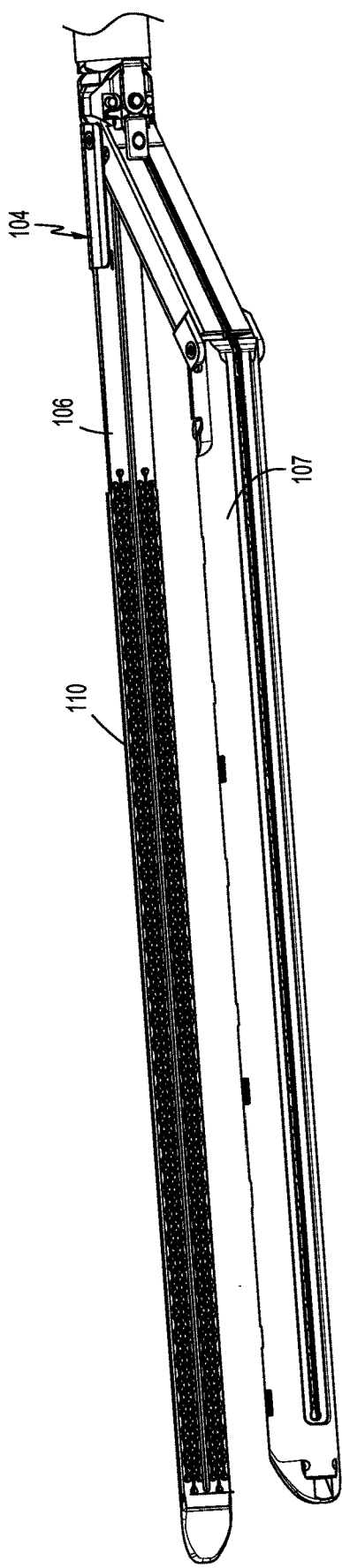
FIG. 4 is a perspective view of the end effector of the reload of FIG. 1.
Figure 5:
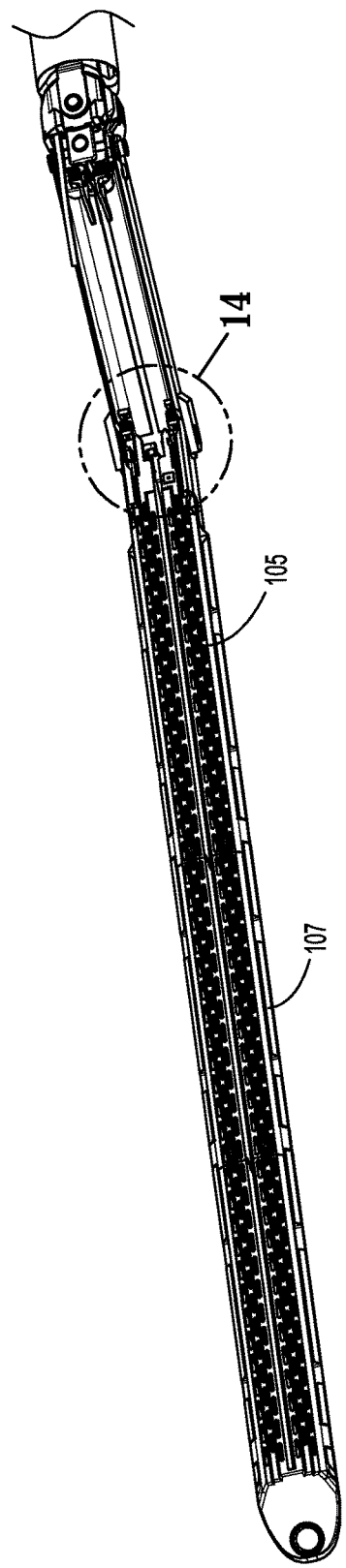
FIG. 5 is a perspective view of the end effector of FIG. 4 with an anvil assembly thereof removed to illustrate a cartridge assembly of the end effector more clearly.
Figure 6:
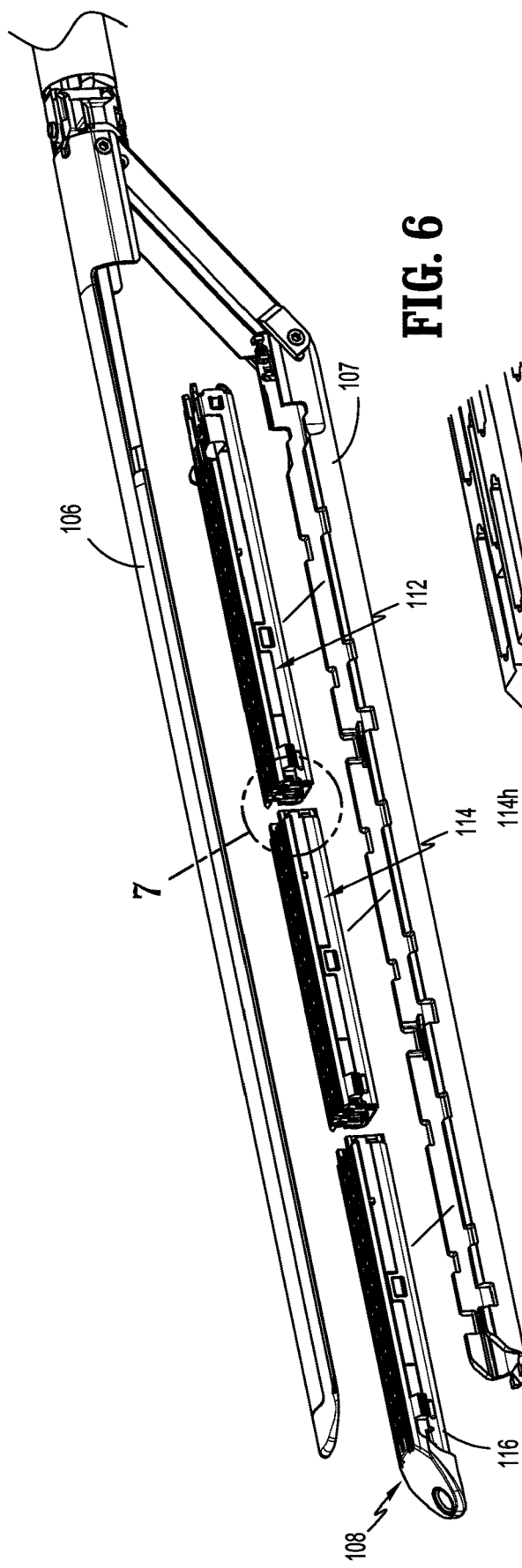
FIG. 6 is a perspective view, with parts separated, of the end effector of FIG. 4.
Figure 7:
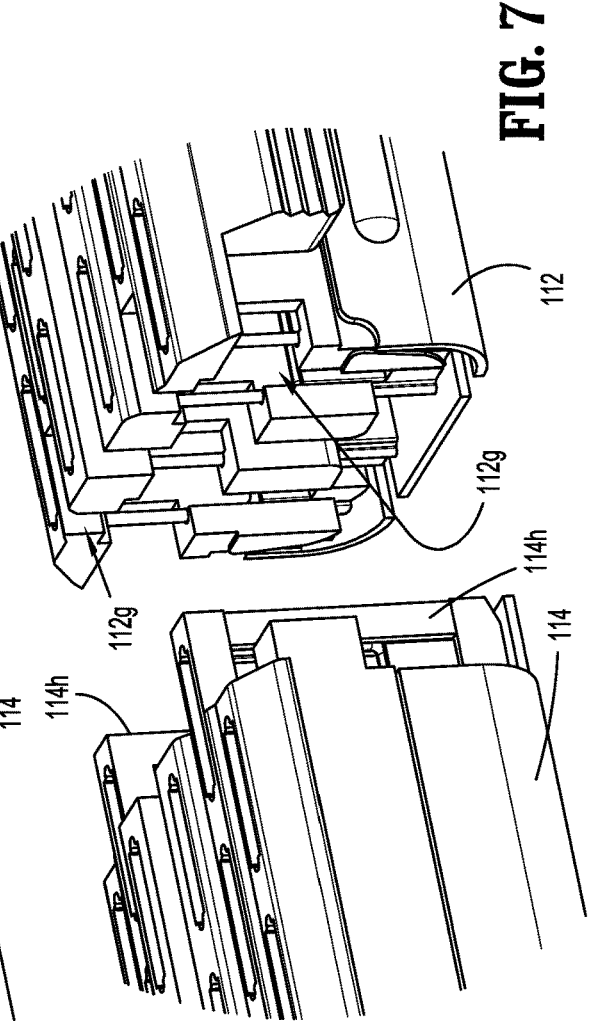
FIG. 7 is an enlarged, perspective view of the indicated area of detail shown in FIG. 6.

Aspects of the disclosed surgical stapling apparatus are described in detail with reference to the drawings, in which like reference numerals designate identical or corresponding elements in each of the several views. As commonly known, the term "clinician" refers to a doctor, a nurse, or any other care provider and may include support personnel. Additionally, the term "proximal" refers to the portion of structure that is closer to the clinician and the term "distal" refers to the portion of structure that is farther from the clinician. In addition, directional terms such as front, rear, upper, lower, top, bottom, and the like are used simply for convenience of description and are not intended to limit the disclosure attached hereto.

As used herein, the terms parallel and perpendicular are understood to include relative configurations that are substantially parallel and substantially perpendicular up to about + or −10 degrees from true parallel and true perpendicular.

In the following description, well-known functions or constructions are not described in detail to avoid obscuring the present disclosure in unnecessary detail.

Briefly, in sleeve gastrectomy procedures, for instance, surgical staplers are used to secure and cut tissue along a long line that requires multiple cartridges of staples before the entirety of the long line is cut and fastened. In particular, after an initial staple cartridge is used, the clinician is required to remove the surgical stapler from the abdomen in order to replace the used cartridge with a new stapler cartridge. The surgical stapler is then reinserted into the abdomen and fired at an adjacent location along the line. The process may be repeated multiple times (e.g., 3-4 times) before the entire length of the line is fastened.

Advantageously, the disclosed surgical stapling apparatus includes a modular reload with three cartridge units that are connected together in series to assist a clinician to perform long lines of cutting and stapling in a single firing (e.g., same firing stroke), such as in a sleeve gastrectomy procedure, instead of firing a single stapler and reloading multiple times, significantly reducing procedure time. Indeed, the disclosed surgical stapling apparatus has a corresponding length anvil that can form the staples of the three cartridge units in the same firing (e.g., in a single firing stroke). More particularly, the disclosed surgical stapling apparatus has an end effector with increased length (e.g., 23-26 cm) compared to a length of an end effector of a typical surgical stapling apparatus (e.g., 60 mm). The disclosed surgical stapling apparatus includes a hinge assembly that enables the end effector to open so that the cartridge units and tissue can be easily loaded.

With reference to FIGS. 1-5, a surgical stapling apparatus 10 of this disclosure includes a housing assembly 12 (which may include one or more handles that may be manually actuatable to fire surgical stapling apparatus 10), an adapter assembly 14 secured to housing assembly 12 and extending distally from housing assembly 12, and a loading unit 100 secured to adapter assembly 14 and extending distally from adapter assembly 14. Adapter assembly 14 and loading unit 100 define a longitudinal axis "X-X" that extends longitudinally therealong. Loading unit 100 may be disposable and/or include one or more disposable components.

Figures 8, 9, 10:
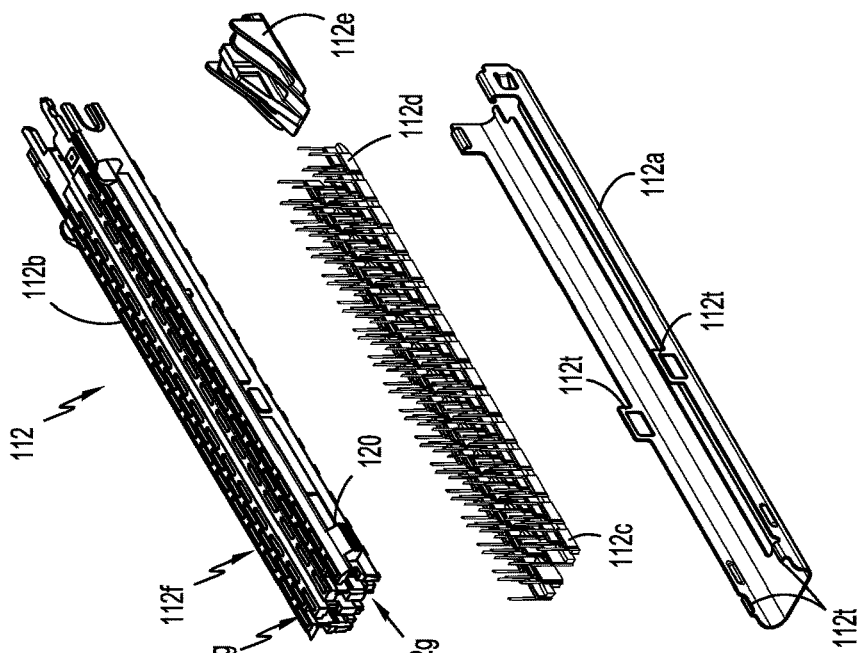
FIG. 8 is a perspective view, with parts separated, of a distal cartridge unit of a reload of the end effector of FIG. 4.
FIG. 9 is a perspective view, with parts separated, of an intermediate cartridge unit of the reload of the end effector of FIG. 4.
FIG. 10 is a perspective view, with parts separated, of a proximal cartridge unit of the reload of the end effector of FIG. 4.
Figure 12:
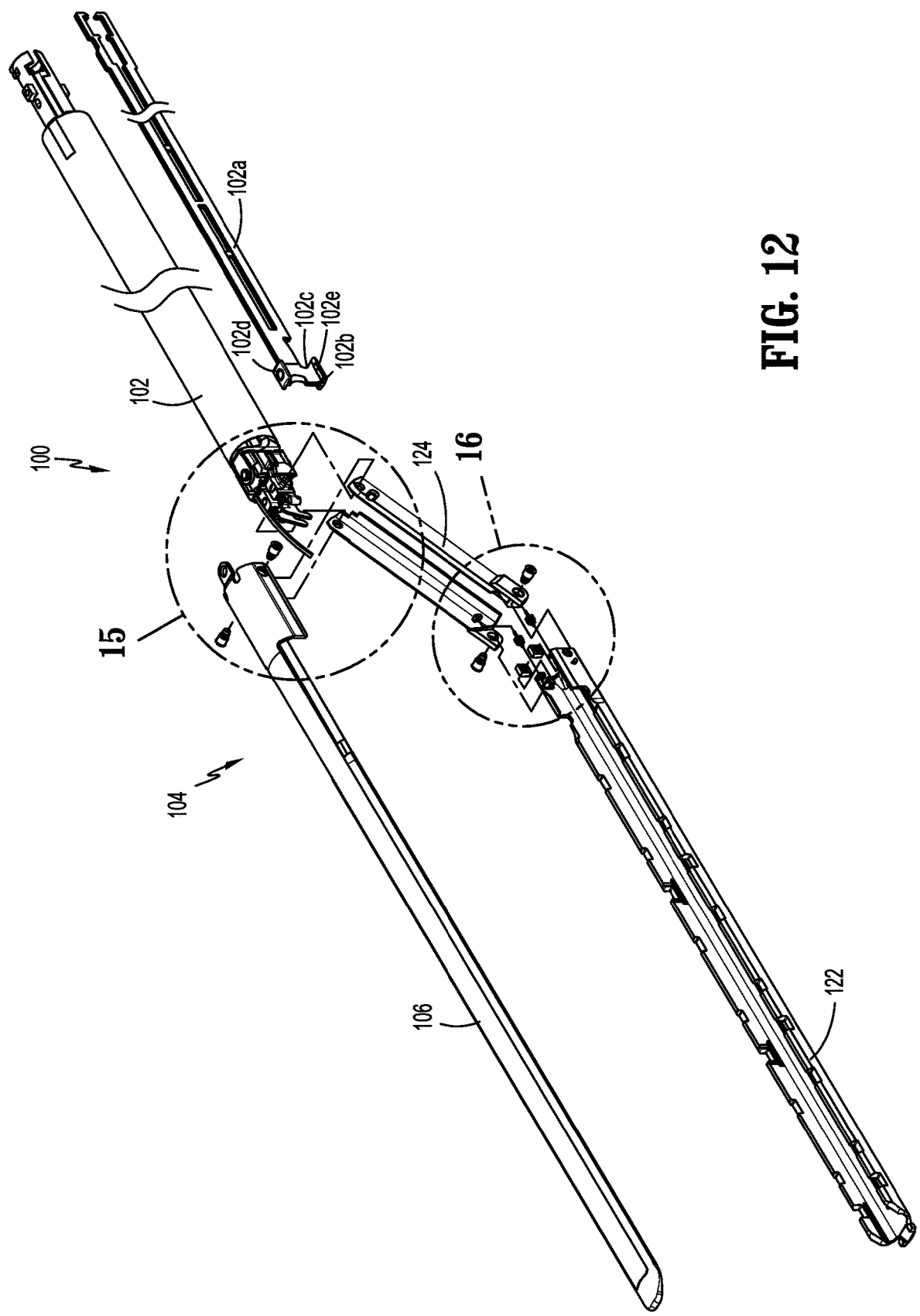
FIG. 12 is a perspective view, with parts separated, of the reload of FIG. 1 with the reload removed therefrom for clarity.
Figure 13:
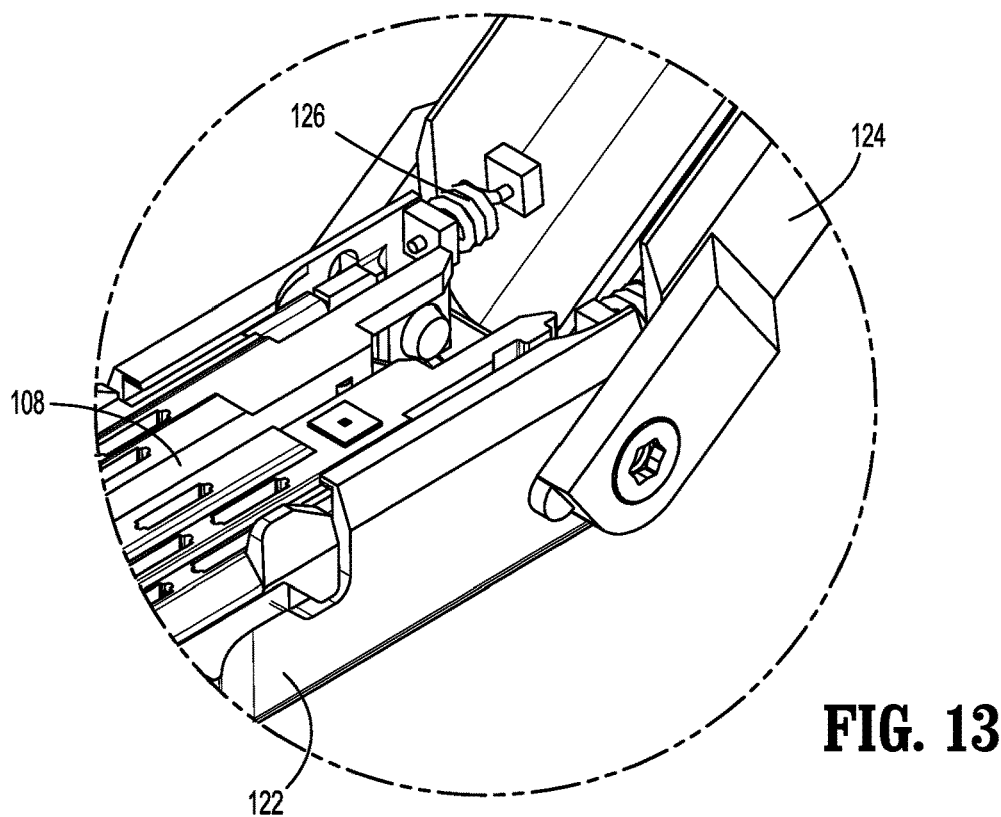
FIG. 13 is an enlarged, perspective view of the indicated area of detail shown in FIG. 2.
Figure 14:
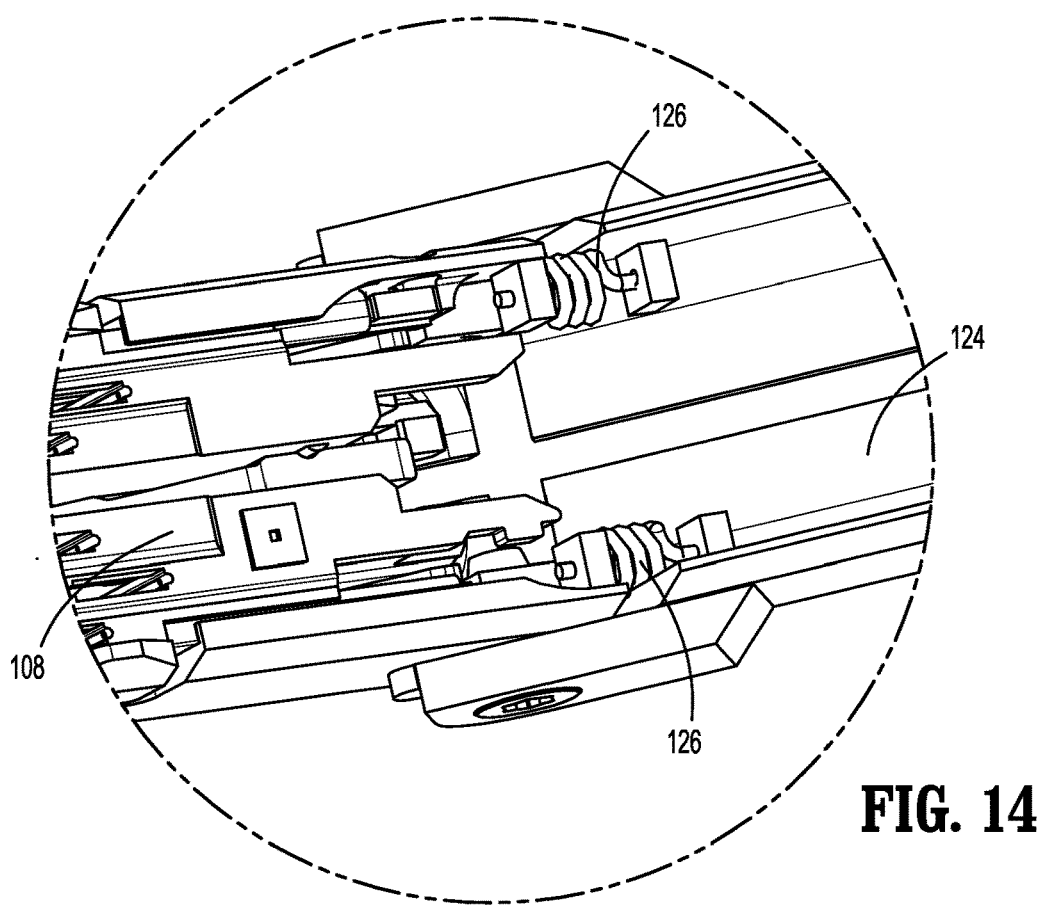
FIG. 14 is an enlarged, perspective view of the indicated area of detail shown in FIG. 5.
Figure 15:
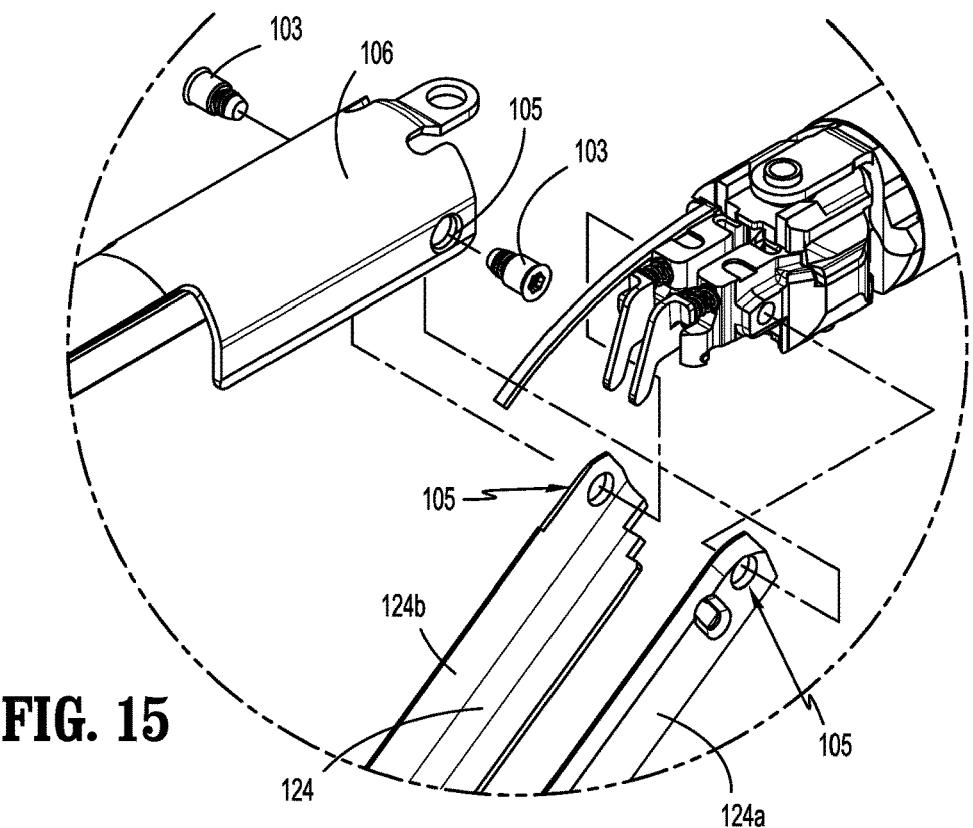
FIG. 15 is an enlarged, perspective view of the indicated area of detail shown in FIG. 12.
Figure 16:
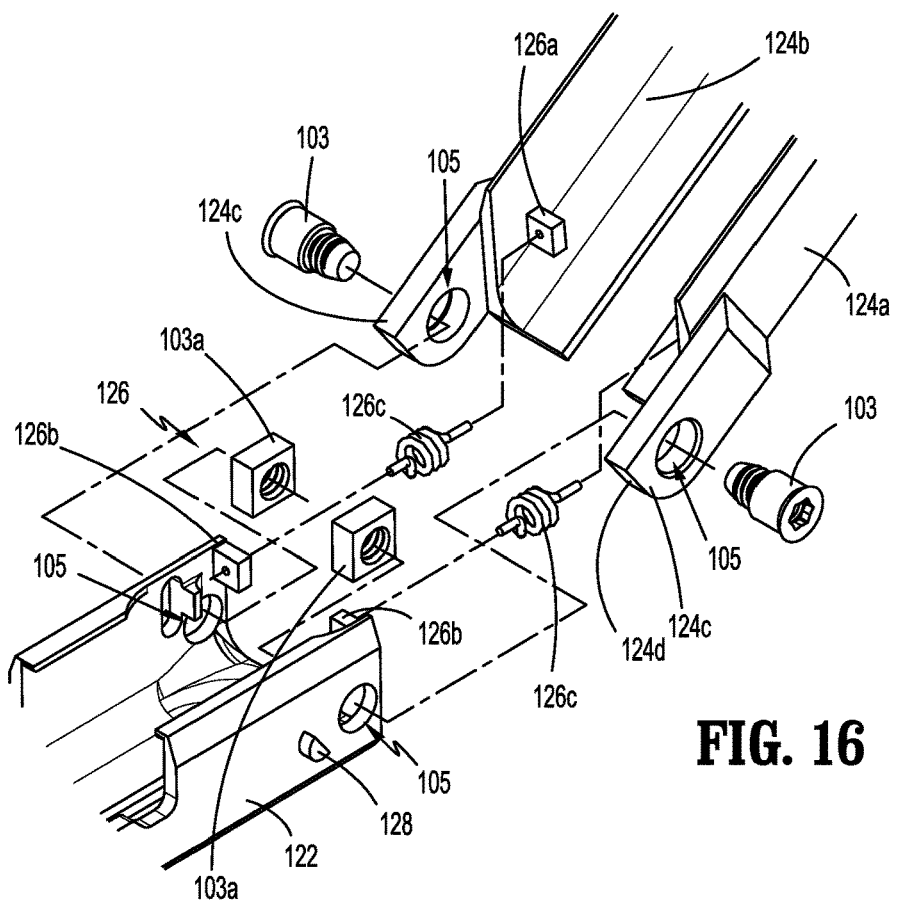
FIG. 16 is an enlarged, perspective view of the indicated area of detail shown in FIG. 12.
Figure 17:
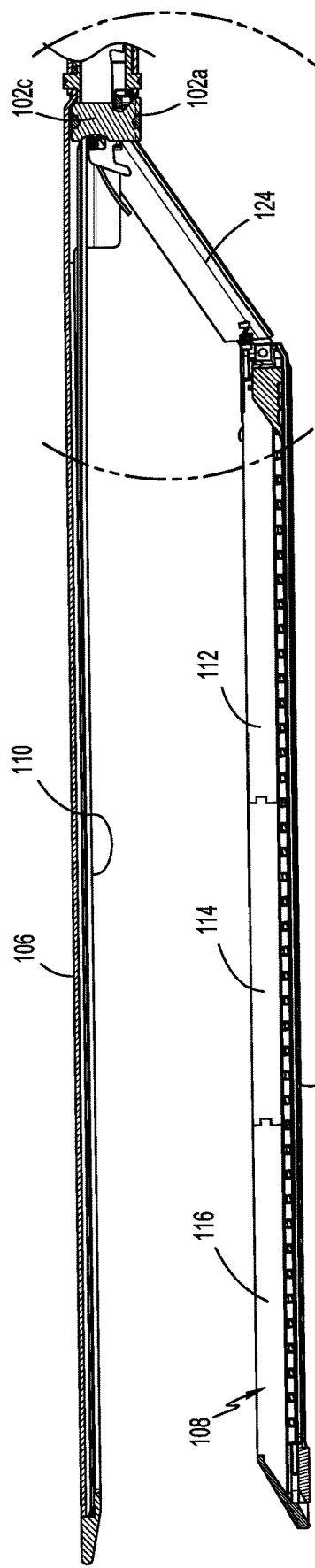
Figure 18:
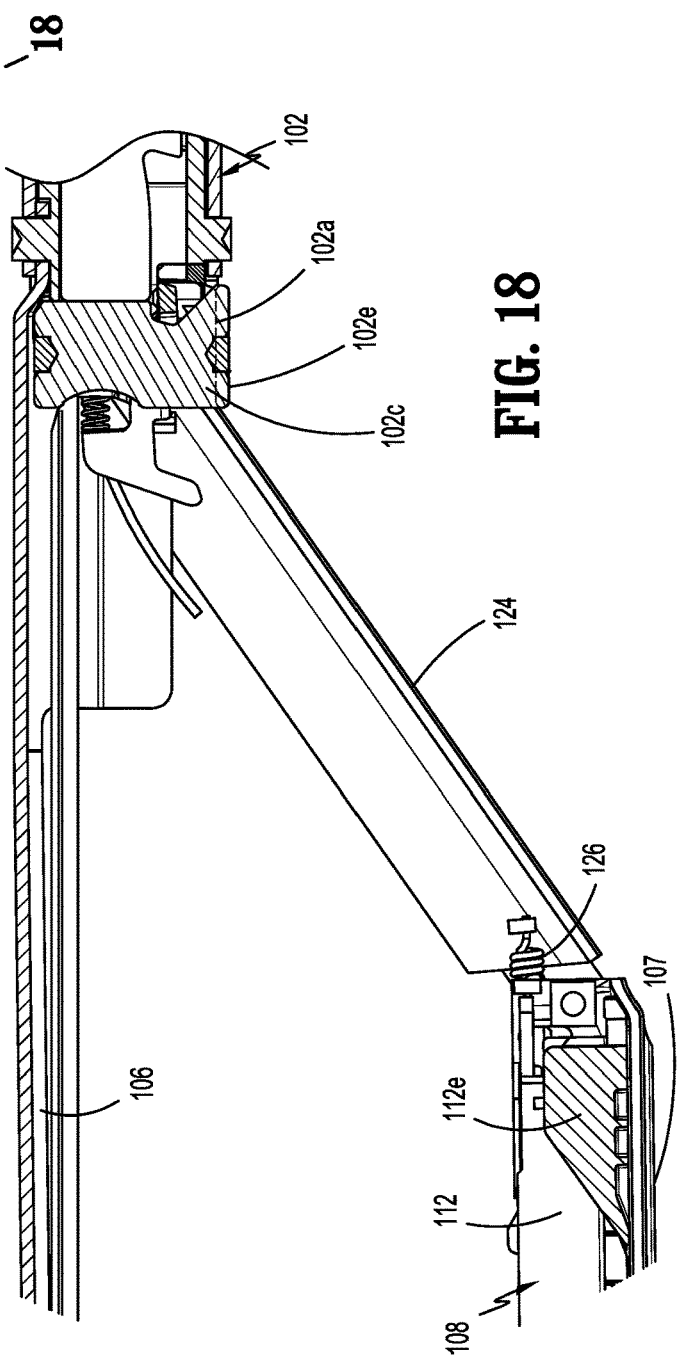
Figure 19:
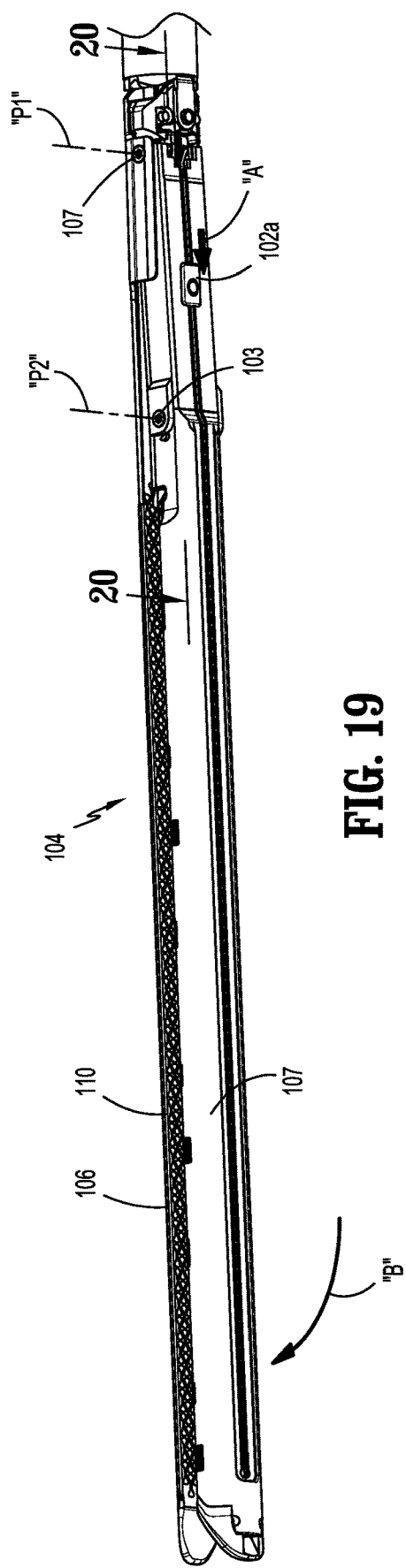
Figure 20:
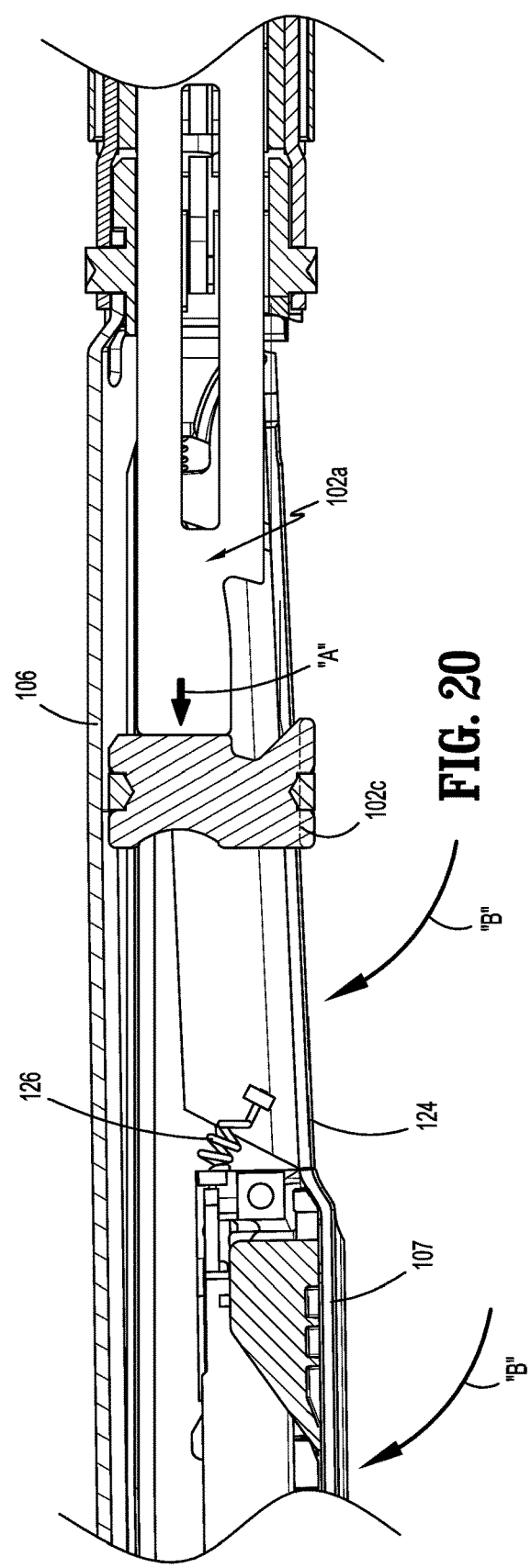

Loading unit 100 of surgical stapling apparatus 10 is releasably secured to a distal end portion of adapter assembly 14 and includes a shaft assembly 102 that supports an end effector 104 on a distal end portion of shaft assembly 102 and a drive beam assembly 102a therein (FIG. 12). End effector 104 includes an anvil assembly 106 and a cartridge assembly 107 that houses a plurality of staples (see, e.g., staples 112d of FIG. 10) in a reload 108 thereof that may be selectively replaceable. Anvil assembly 106 includes an anvil 110 against which the plurality of staples is formed upon a firing of surgical stapling apparatus 10.

For a more detailed description of similar stapling apparatus, or components thereof, reference can be made, for example, to U.S. Pat. No. 9,713,470 to Scirica et al. and U.S. Pat. No. 8,070,033 to Milliman et al., the entire contents of each of which are incorporated herein by reference.

Turning now to FIGS. 6-11, reload 108 of cartridge assembly 107 includes a proximal cartridge unit 112, an intermediate cartridge unit 114, and a distal cartridge unit 116 which are separate and distinct cartridge units that connect together via tongue-and-groove arrangements to form a unitary structure.

Proximal cartridge unit 112 of reload 108 includes a proximal cartridge base 112a that secures to a proximal cartridge 112b via tabs 112t and supports a plurality of rows of proximal pushers 112c, a plurality of rows of proximal staples 112d, and a sled 112e that is distally advanceable through reload 108 upon a firing of surgical stapling apparatus 10. Proximal cartridge 112b has a tissue contacting surface that defines staple retention slots 112f in registration with proximal staples 112d. Proximal cartridge 112b further defines distal grooves 112g in a distal end thereof. Sled 112e is positioned to advance distally through proximal cartridge unit 112 to drive pushers 112c upwardly and cause staples 112d to fire through staple retention slots 112f defined in proximal cartridge 112b as sled 112e translates therealong.

Intermediate cartridge unit 114 of reload 108 includes an intermediate cartridge base 114a that secures to an intermediate cartridge 114b via tabs 114t and supports a plurality of rows of intermediate pushers 114c and a plurality of rows of intermediate staples 114d. Intermediate cartridge 114b defines staple retention slots 114f in registration with intermediate staples 114d for enabling sled 112e of reload 108 to fire intermediate staples 114d through staple retention slots 114f when sled 112e advances distally along intermediate cartridge unit 114 and into engagement with pushers 114c. Intermediate cartridge unit 114 further defines distal grooves 114g in a distal end thereof and includes proximal tongues 114h extending from a proximal end portion thereof. Proximal tongues 114h are configured to be received within distal grooves 112g of proximal cartridge unit 112 for securing intermediate and proximal cartridge units 114, 116 together.

Distal cartridge unit 116 of reload 108 includes a distal cartridge base 116a that secures to a distal cartridge 116b via tabs 116t and supports a plurality of rows of distal pushers 116c and a plurality of rows of distal staples 116d. Distal cartridge 116b defines staple retention slots 116f in registration with distal staples 116d for enabling sled 112e of reload 108 to fire distal staples 116d through staple retention slots 116f when sled 112e advances distally along distal cartridge unit 116 and into engagement with pushers 116c. Distal cartridge unit 116 includes proximal tongues 116h extending from a proximal end portion thereof. Proximal tongues 116h are configured to be received within distal grooves 114g of intermediate cartridge unit 114 for securing distal and intermediate cartridge units 116, 114 together. Distal cartridge unit 116 extends distally to a blunt distal tip 116g.

Figure 11:
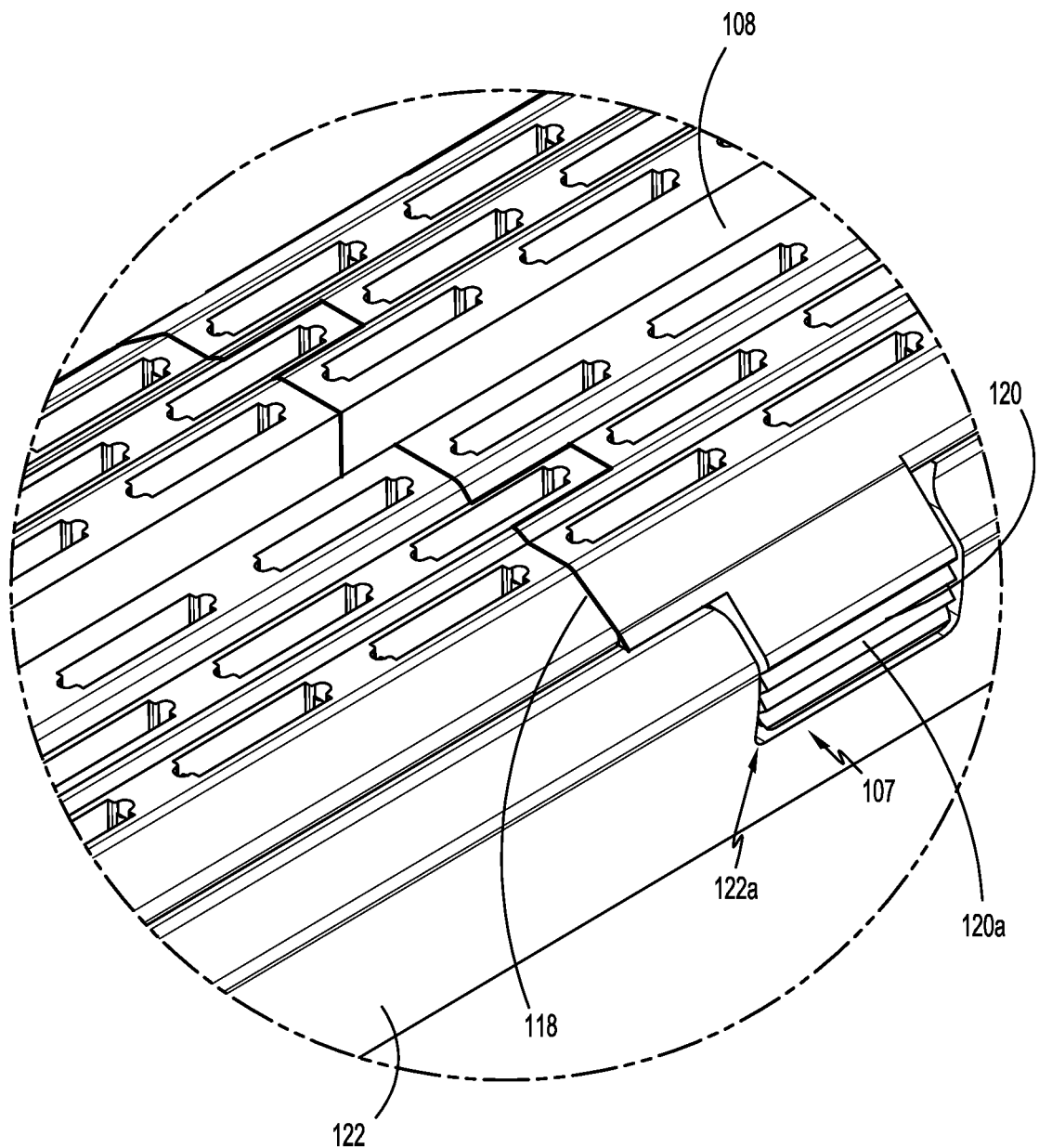
FIG. 11 is an enlarged, perspective view of the indicated area of detail shown in FIG. 2.

As seen in FIG. 11, proximal, intermediate, and distal cartridge units 112, 114, 116 define a castellated seam 118 that separates the respective cartridge units when connected together. Further, each of proximal, intermediate, and distal cartridges 112b, 114b, 116b include a sidelocks 120 that extends from a side surface thereof for facilitating securement to cartridge assembly 107. Sidelocks 120 are positioned to seat in sidewall grooves 122a defined in a cartridge channel 122 of cartridge assembly 107 at spaced-apart locations along cartridge assembly 107 to facilitate autolocation thereof. Each sidelock 120 includes a plurality of ridges 120a to facilitate finger gripping for selectively removing a respective one of the proximal, intermediate, and distal cartridge units 112, 114, 116 from cartridge assembly 107 and/or from one of the other cartridge units.

Turning now to FIGS. 12-16, anvil and cartridge assemblies 106, 107 of end effector 104 are pivotally coupled to the distal end portion of shaft assembly 102 with threaded fasteners 103 such as shoulder bolts or socket cap screws, secured to openings 105 defined through sidewalls thereof. Anvil and cartridge assemblies 106, 107 are positioned to receive drive beam assembly 102a therethrough to move the anvil and cartridge assemblies 106, 107 between open and closed positions, to fire the reload 108 supported by the cartridge assembly 107, and to cut tissue clamped between the anvil and cartridge assemblies 106, 107 with a knife 102b supported on an I-beam 102c of drive beam assembly 102a as drive beam assembly 102a advances sled 112e through anvil and cartridge assemblies 106, 107 upon a firing of surgical stapling apparatus 10. I-beam 102c includes upper and lower flanges 102d, 102e that engage anvil and cartridge assemblies 106, 107 to enable anvil and cartridge assemblies 106, 107 to move from the open position to the closed position.

Cartridge assembly 107 includes the cartridge channel 122, a hinge assembly 124 and a spring mechanism 126 supported between hinge assembly 124 and cartridge channel 122. Hinge assembly 124 pivotally couples cartridge channel 122 to the distal end portion of shaft assembly 102 to enables the end effector 104 to open so that the cartridge units 112-116 and tissue can be easily loaded between the anvil and cartridge assemblies 106, 107. Hinge assembly 124 includes a first arm 124a and a second arm 124b that are laterally spaced apart (e.g., by gap) to receive a drive beam assembly 102a therebetween. Hinge assembly 124 is movable between a first position in which first and second arms 124a, 124b are disposed at an angle (e.g., transverse) relative to longitudinal axis "X" (corresponding to the open or unclamped position of end effector 104) and a second position in which first and second arms 124a, 124b are parallel to longitudinal axis "X" (corresponding to the closed or clamped position of end effector 104). First and second arms 124a, 124b have proximal end portions pivotally coupled to the distal end portion of shaft assembly 102 and proximal end portion of anvil assembly 106 by threaded fasteners 103 and nuts 103a. First and second arms 124a, 124b have distal end portions pivotally coupled to a proximal end portion of cartridge channel 122 via threaded fasteners 103 received through openings 105 defined through proximal end portion of cartridge channel 122 and openings 105 defined through distal end portions of first and second arms 124a, 124b. First and second arms 124a, 124b also include engagement wings 124c that extend from the distal end portion of first and second arms 124a, 124b. Engagement wings 124c include a abutment surfaces 124d positioned to engage angled stoppers 128 extending from the outer sidewalls of the proximal end portion of cartridge channel 122. Stoppers 128 are configured to contact abutment surfaces 124d of engagement wings 124c to prevent cartridge assembly 107 from inverting when end effector 104 is disposed in the open position. Spring mechanism 126 is configured to urge cartridge assembly 107 toward a parallel position relative to anvil assembly 106 when end effector 104 is in the open position. Spring mechanism 126 includes arm mounts 126a secured on the distal end portion of first and second arms 124a, 124b, channel mounts 126b secured on the proximal end portion of cartridge channel 122, and tension springs 126c secured at opposite ends to arm mounts 126a and channel mounts 126b.

Turning now to FIGS. 17-23, in use, for example in a sleeve gastrectomy procedure, when surgical stapling apparatus 10 is fired, drive beam assembly 102a advances distally along hinge 124, as indicated by arrows "A," so that flange 102e of I-beam 102c slides along the bottom surfaces of first and second arms 124a, 124b of hinge assembly 124. As drive beam assembly 102a advances distally along hinge assembly 124, drive beam assembly 102a causes hinge assembly 124 to pivot about pivot axes "P1" and "P2" defined through fasteners 103 of end effector 104 so that cartridge assembly 107 pivots toward anvil assembly 106, as indicated by arrows "B," from the open position to the closed position to clamp tissue therebetween. The drive beam assembly 102a can be drawn proximally to, for example, readjust tissue between the anvil and cartridge assemblies 106, 107 and/or a stapling area. Spring mechanism 126 and stopper 128 are positioned to relative to one another to prevent cartridge assembly 107 from inverting (e.g., about pivot axis "P2") and to maintain the anvil and cartridge assemblies 106, 107 in parallel relation with one another between the open and closed positions of end effector 104. With I-beam 102*c* of drive beam assembly 102*a* positioned distally beyond hinge assembly 124 and in contact with sled 112*e* in reload 108, end effector 104 is disposed in the closed position (see FIGS. 21 and 22). Continued distal advancement of drive beam assembly 102*a*, as indicated by arrow "C," causes drive beam assembly 102*a* to distally drive sled 112*e* through reload 108 so that the staples of reload 108 can be sequentially fired as knife 102*b* of I-beam 102*c* cuts the clamped and fastened tissue disposed between the anvil and cartridge assemblies 106, 107.

Further, although illustrated and described in connection with an endoscopic linear surgical stapling apparatus, the disclosed loading unit arrangement may be utilized on any suitable surgical stapling apparatus such as an open surgical stapling apparatus, a transverse surgical stapling apparatus, and/or a circular stapling apparatus, any of which may be powered or manual apparatus.

Securement of any of the components of the presently disclosed apparatus may be effectuated using known securement techniques such welding, crimping, gluing, fastening, etc.

The various aspects disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients. For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary aspects, and that the description, disclosure, and figures should be construed merely as exemplary of particular aspects. It is to be understood, therefore, that the present disclosure is not limited to the precise aspects described, and that various other changes and modifications may be effected by one skilled in the art without departing from the scope or spirit of the disclosure. Additionally, the elements and features shown or described in connection with certain aspects may be combined with the elements and features of certain other aspects without departing from the scope of the present disclosure, and that such modifications and variations are also included within the scope of the present disclosure. Accordingly, the subject matter of the present disclosure is not limited by what has been particularly shown and described.

What is claimed is:

1. A loading unit for a surgical stapling apparatus, the loading unit comprising:
    a shaft assembly;
    an end effector defining a longitudinal axis, the end effector secured to the shaft assembly and including:
        an anvil assembly;
        a cartridge assembly including a cartridge channel and a hinge assembly pivotally coupled together, the hinge assembly including at least one arm that extends between the shaft assembly and the cartridge channel to enable the cartridge assembly to move relative to the anvil assembly between an open position and a closed position, the cartridge assembly including a reload that is selectively attachable to the cartridge channel, the reload having a plurality of cartridge units, each cartridge unit being longitudinally offset from the other cartridge units when the cartridge units are attached to the cartridge channel; and
        a drive beam assembly that is positioned to advance distally through the anvil and cartridge assemblies to move the cartridge assembly relative to the anvil assembly.

2. The loading unit of claim 1, wherein the plurality of cartridge units selectively interconnect with one another.

3. The loading unit of claim 2, wherein each cartridge unit of the plurality of cartridge units includes a plurality of rows of staples.

4. The loading unit of claim 2, wherein the plurality of cartridge units interconnect by a tongue- and-groove arrangement.

5. The loading unit of claim 2, wherein at least one cartridge unit of the plurality of cartridge units includes a side lock that secures the at least one cartridge unit to the cartridge channel.

6. The loading unit of claim 1, further comprising a spring mechanism that extends between the hinge assembly and the cartridge channel to prevent the cartridge assembly from inverting.

7. The loading unit of claim 1, wherein the cartridge channel includes a stopper that is positioned to engage the hinge assembly to maintain the cartridge assembly in parallel relation to the anvil assembly.

8. The loading unit of claim 1, wherein the hinge assembly further includes at least one fastener that connects the at least one arm to the shaft assembly, the least one arm positioned to pivot about the least one fastener.

9. An end effector for a surgical stapling apparatus, the end effector defining a longitudinal axis and comprising:
    an anvil assembly;
    a cartridge assembly including a cartridge channel supporting a reload, the reload including a plurality of separate and distinct cartridge units that removably interconnect with one another within the cartridge channel such that each cartridge unit is longitudinally offset from the other cartridge units;

a drive beam assembly that is positioned to advance distally through the anvil and cartridge assemblies to move the cartridge assembly relative to the anvil assembly;

a hinge assembly that is pivotally coupled to a proximal end portion of the cartridge channel; and wherein the cartridge channel includes a stopper that is positioned to engage the hinge assembly to maintain the cartridge assembly in parallel relation to the anvil assembly.

10. The end effector of claim 9, each cartridge unit of the plurality of separate and distinct cartridge units includes a plurality of rows of staples.

11. The end effector of claim 10, wherein a first cartridge unit of the plurality of separate and distinct cartridge units includes a sled that is positioned to advance through each cartridge unit of the plurality of separate and distinct cartridge units to fire the plurality of rows of staples in each cartridge unit.

12. The end effector of claim 9, wherein the hinge assembly includes a first arm and second arm, the first arm coupled to a first side of the cartridge channel by a first fastener, the second arm coupled to a second side of the cartridge channel by a second fastener.

13. The end effector of claim 9, wherein a first cartridge unit of the plurality of separate and distinct cartridge units is coupled to a second cartridge unit plurality of separate and distinct cartridge units by a castellated seam.

14. The end effector of claim 13, wherein the first cartridge unit includes at least one groove and the second cartridge unit includes at least one tongue, the at least one groove positioned to receive the at least one tongue therein to define the castellated seam.

15. The end effector of claim 9, further comprising a spring mechanism that extends between the hinge assembly and the cartridge channel to prevent the cartridge assembly from inverting.

16. A surgical stapling apparatus, comprising:

a shaft assembly defining a longitudinal axis;

a drive beam assembly supported in the shaft assembly;

an anvil assembly; and a cartridge assembly pivotally coupled to the anvil assembly and to the shaft assembly by a hinge assembly, the cartridge assembly supporting a reload having a plurality of separate and distinct cartridge units that are independently separable from one another and longitudinally offset from one another, each cartridge unit of the plurality of separate and distinct cartridge units including a plurality of staples positioned to form against the anvil assembly, wherein in response to the drive beam assembly translating through the hinge assembly, the hinge assembly pivots from a first position transverse to the longitudinal axis of the shaft assembly to a second position in parallel relation to the longitudinal axis, the drive beam assembly being positioned to advance distally through the anvil and cartridge assemblies to move the cartridge assembly relative to the anvil assembly.

\* \* \* \* \*